United States Patent
Zambaux (10) Patent No.: US 8,950,579 B2
(45) Date of Patent: Feb. 10, 2015

(54) STERILIZED OR DEPYROGENED PACKAGING

(75) Inventor: Jean-Pascal Zambaux, Audenge (FR)

(73) Assignee: Pall Life Sciences Belgium BVBA, Hoegaarden (BE)

( * ) Notice: Subject to any disclaimer, the term of this patent is extended or adjusted under 35 U.S.C. 154(b) by 12 days.

(21) Appl. No.: 13/257,554

(22) PCT Filed: Mar. 19, 2010

(86) PCT No.: PCT/EP2010/053617
§ 371 (c)(1),
(2), (4) Date: Sep. 19, 2011

(87) PCT Pub. No.: WO2010/106168
PCT Pub. Date: Sep. 23, 2010

(65) Prior Publication Data
US 2012/0006717 A1    Jan. 12, 2012

(30) Foreign Application Priority Data

Mar. 20, 2009   (EP) .................................... 09305251

(51) Int. Cl.
*A61L 2/26*   (2006.01)
*A61L 2/04*   (2006.01)
*B65B 31/04*  (2006.01)
*B65B 55/02*  (2006.01)

(52) U.S. Cl.
CPC ... *A61L 2/04* (2013.01); *A61L 2/26* (2013.01); *B65B 31/04* (2013.01); *B65B 55/02* (2013.01)

USPC .......................................... 206/438; 422/294

(58) Field of Classification Search
CPC ...... A61L 2/0094; A61L 2/20; A61L 2202/10; A61L 2202/11; A61L 2202/122; G01K 5/48
USPC .......... 206/438, 6; 422/28, 33, 26, 295, 243, 1
See application file for complete search history.

(56) References Cited

U.S. PATENT DOCUMENTS

| | | | |
|---|---|---|---|
| 4,416,417 A | | 11/1983 | Sanderson et al. |
| 4,549,717 A | | 10/1985 | Dewaegheneire |
| 5,255,809 A | | 10/1993 | Ervin et al. |
| 5,540,901 A | * | 7/1996 | Riley ............................ 422/300 |
| 7,455,668 B2 | * | 11/2008 | Petrakis ..................... 604/890.1 |
| 7,523,827 B2 | * | 4/2009 | Dane et al. ..................... 206/503 |
| 8,298,054 B2 | | 10/2012 | Hodge et al. |
| 2004/0060260 A1 | | 4/2004 | Gottlieb et al. |
| 2006/0255064 A1 | | 11/2006 | Donaldson |
| 2006/0283856 A1 | * | 12/2006 | Spinelli et al. ................ 220/201 |
| 2007/0014686 A1 | * | 1/2007 | Arnold et al. ................... 422/28 |
| 2007/0225785 A1 | * | 9/2007 | Park et al. ..................... 607/116 |
| 2012/0031042 A1 | | 2/2012 | Zambaux |

(Continued)

FOREIGN PATENT DOCUMENTS

| DE | 102007002105 | 7/2008 |
|---|---|---|
| EP | 0 201 994 | 5/1985 |

(Continued)

*Primary Examiner* — Anthony Stashick
*Assistant Examiner* — Ernesto Grano
(74) *Attorney, Agent, or Firm* — King & Schickli, PLLC (57) ABSTRACT

The invention relates mainly to a packaging which may be sterilized and/or depyroged. The invention relates in particular to a packaging for the sterilization or pyrogen free packaging for one or more packaged devices, said packaging comprising a valve or outlet tube.

36 Claims, 3 Drawing Sheets

(56) References Cited

U.S. PATENT DOCUMENTS

| | | |
|---|---|---|
| 2012/0107174 A1 | 5/2012 | Zambaux |
| 2012/0294697 A1 | 11/2012 | Zambaux |
| 2013/0017131 A1 | 1/2013 | Galliher et al. |

FOREIGN PATENT DOCUMENTS

| | | |
|---|---|---|
| JP | H05-74538 U | 10/1993 |
| JP | 2000-024098 | 1/2000 |
| WO | WO2008/084047 | 7/2008 |
| WO | 2012013910 A1 | 7/2011 |

* cited by examiner

STERILIZED OR DEPYROGENED PACKAGING

The invention relates mainly to a sterilized and/or depyroged packaging. The invention relates in particular to a sterilized and/or depyroged packaging comprising a valve.

STATE OF THE ART

The prior art discloses trays for vials or containers which may be sterilized and/or depyroged.

Now a day, depyrogenation of vials or containers is performed by washing the vials or containers and putting them into a tunnel or tube under a laminar flow at a temperature of at least 253° C. At the end of said tunnel or tube the vials or containers are cooled (or get cooled) and are filled by the desired product under a laminar flow before their sealing.

For a small number of vials or container depyrogenation, two procedures exist: the depyrogenation is performed:
- Either through a passage of the vials or containers in an oven connected to an isolator for performing in the isolator the filling by the desired product under controlled atmosphere; or
- Through a passage of the vials or containers in an oven, the vials or containers being plugged or sealed under a laminar flow after depyrogenation. Then the vials or containers are got out of the oven. Before using these vials or containers, a further stay in an autoclave is necessary before opening the vials or containers and their filling.

These procedures are costly and time consuming for the manufacturer who wants to fill vials or containers.

The prior art does not solve many problems identified by the present inventors.

GOAL OF THE INVENTION

This procedure is not adapted to the pharmaceutical industry, where a small number of vials or containers or of one or more packaged devices have to be used. The prior art does not respond to need from the pharmaceutical/medical industry notably in case of clinical assays, or clinical studies, or clinical approval procedures. The prior art does not respond to the skilled person's need where no material, such as a sterilizer or depyrogenation apparatus, is available for performing such a sterilization or depyrogenation. This is the case of hospitals and dental offices. The same need exists before surgical treatments/operations.

The present invention aims to solve the technical problem of providing a device which may be easily sterilized and/or freed from pyrogen (depyrogened). This device is typically a packaging for one or more packaged devices such as containers or vials or other instruments or devices, in particular for use in an industrial field or market where a sterilized or pyrogen free (depyrogened) packaging is needed.

Accordingly, the invention aims to provide such device for the chemical, the food, the pharmaceutical, and/or the medical industry.

The invention aims to solve the new technical problem of providing a ready-to-use packaging of pyrogen free instruments, devices, or vials or containers.

DESCRIPTION OF THE INVENTION

The present invention relates to a device or packaging which may be sterilized and/or depyroged, i.e. freed from pyrogens.

A pyrogen is a substance that induces fever. The terms "pyrogen free" mean that pyrogen are not present or below acceptable standard for the use of the specific device or packaging according to the invention. "Depyrogenation" refers to the removal of pyrogens from a device or composition, most commonly from injectable pharmaceuticals and from pharmaceutical or medical devices; and for surgical or dental materials or instruments. "Sterilization" refers to any process that effectively kills or eliminates transmissible agents (such as fungi, bacteria, viruses, spore forms, etc.) from a surface, equipment, article of food or medication, or biological culture medium.

The device or packaging of the invention is according to one embodiment a packaging, in particular for use in an industrial field or market where a sterilization or pyrogen free packaging is needed. In one embodiment, the device of the invention is a packaging for the chemical, the food, the pharmaceutical, and/or the medical industry. In one embodiment, the device of the invention is a packaging for containers or vials, or for other instruments or devices such as prosthesis, implants, surgical or dental materials or instruments.

The invention relates to a packaging made of one or more materials which do not degrade at a sterilization or depyrogenation temperature said packaging comprising a packaging outlet and an outlet tube connected to said packaging outlet, said outlet tube comprising a proximal end and a distal end, said outlet tube comprising between the proximal end and the distal end a closing means made partly or completely of a shape memory material. According to the invention said closing means may be fixed or not to the outlet tube. Said closing means may be manufactured separately from the packaging and then placed on/in the outlet tube between the outlet distal and proximal ends. "Between the ends" mean not at the ends. "A closing means" refers also to one or more closing means. Thus the device of the invention may comprise several closing means made partly or completely of a shape memory material.

Said outlet tube is forming a passageway for a fluid, and in particular for a gas contained in the packaging.

In one embodiment, said closing means is in a closed position when the temperature is below a reference temperature (closing temperature or Tc) for closing the outlet tube so that a gas may not penetrate into the packaging through said packaging outlet. In another embodiment, said closing means is in an open position when the temperature is above said reference temperature (closing temperature) for allowing a gas going into said packaging by passing through the packaging outlet.

The terms "closed position" mean a position closing the outlet tube so that a fluid outside said packaging may not penetrate into the packaging through said packaging outlet. The terms "open position" mean that a fluid contained in the packaging may go into said packaging through said outlet tube proximal end.

The closing means is working as a valve, and may be called "a valve".

In one embodiment, said shape memory material is a shape memory alloy.

In one embodiment, said packaging is a bag for containing a tray of vials or containers or other instruments or devices. Said bag may be partly or fully flexible. Said completely or partly flexible bag may be made of a plastic material, as described below. Said flexibility may be obtained by using a plastic polymer film or sheet. Examples of such polymers are given in the description (PEEK, PFA, etc). Said tray is placed inside said bag.

In one embodiment said bag is thermosealed or laser sealed after said tray is placed inside the bag. In another embodiment said bag includes a surface hole for introducing a tray or other instruments or devices, inside said packaging. Said surface hole may be closed by a removable film or sheet covering the vials or containers or other instruments or devices. The removable film or sheet may be sealed to the packaging surface to cover up the surface hole.

In one embodiment, said packaging is forming a tray for vials or containers or for other instruments or devices, said tray comprising side walls, a bottom wall and a completely or partly open top surface defining an inside packaging area and an outside packaging area, wherein at least one wall or top surface comprises an outlet to which is connected an outlet tube to let a gas pass through said outlet, wherein said outlet tube comprises a proximal end and a distal end, said outlet tube comprising between the proximal end and the distal end a closing means made partly or completely of a shape memory material, said closing means closing the outlet tube, said packaging optionally comprising a removable sheet or film placed on the tray top surface to isolate the inside packaging area from the outside packaging area.

A tray may be partly or fully rigid (rigid material), in whole or in part (some rigid part and flexible parts).

Said packaging may comprise a support area for locating and supporting vials or containers or other instruments or devices. Said support area optionally includes separate compartments, wherein each vial or container, instrument or device, may be located in a separate compartment.

In one embodiment, the removable sheet or film is made of a thermoplastic material and bonded together with the tray by heat sealing the thermoplastic material along the outer edge or periphery of the top surface packaging. The foregoing thermal seal or seam may extend entirely around the periphery of the tray.

The closing means is made partly or completely made from a shape memory material. Examples of said shape memory materials are shape memory alloys (temperature dependent shape memory alloy), such as copper-based or NiTi (nickel and titanium)-based shape memory alloys, or copper-zinc-aluminum-nickel alloys; copper-aluminium-nickel alloys. This includes Ni—Ti (~55% Ni) and Nitinol. Shape memory alloys includes also alloys selected from the group consisting of Ag—Cd (44/49 at. % Cd) ; Au—Cd (46.5/50 at. % Cd); Cu—Al—Ni (14/14.5 wt. % Al and 3/4.5 wt. % Ni); Cu—Sn (approx. 15 at. % Sn); Cu—Zn (38.5/41.5 wt. % Zn); Cu—Zn—X (X=Si, Al, Sn); Fe—Pt (approx. 25 at. % Pt); Mn—Cu (5/35 at. % Cu); Fe—Mn—Si; Pt alloys; Co—Ni—Al; Co—Ni—Ga; Ni—Fe—Ga; and Ti—Pd alloys in various concentrations. Suitable alloys are those which shape is different below the closing temperature than above the closing temperature.

Said closing means may present various shape as long as said shape may compress or squeeze the outlet tube to stop the passage of a gas from the packaging outside to the packaging inside through the outlet tube proximal end in a closed position, and let a gas pass through the outlet tube in an open position.

Figure 1A:
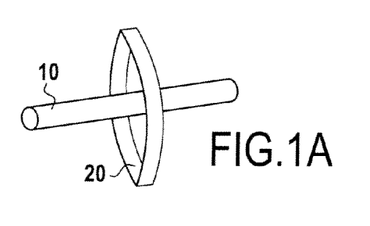
FIG. 1 represents a schematic perspective of one embodiment of the shape memory closing means placed on the outlet tube.
Figure 1B:
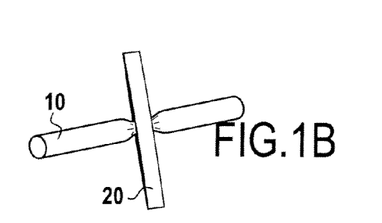

In one embodiment, said closing means (20) is placed around the outlet tube (10) between said proximal and distal end to close the outlet tube (10) by compression or squeezing when said closing means (20) is in closed position (FIG. 1B) and when said closing means (20) is in an open position the outlet tube (10) is not compressed or squeezed to let a gas pass through the outlet tube from the proximal end to the distal end (FIG. 1A). Said closing means may be a clamp clamping the outlet tube.

Figure 2A:
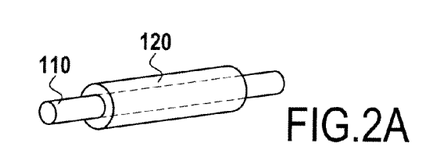
FIG. 2 represents a schematic perspective of another embodiment of shape memory closing means placed on the outlet tube.
Figure 2B:
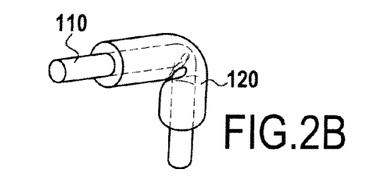

In one embodiment, said closing means (120) in an open position presents a ring, a oval, or a U-shape, or presents a tubular shape surrounding the outlet tube (110) so that the outlet tube is opened (FIG. 2A), and said closing means, in a closed position, compresses or squeezes the outlet tube to close the outlet tube (FIG. 2B).

Figure 3A:
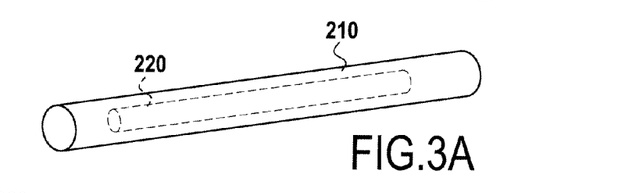
FIG. 3 represents a schematic perspective of another embodiment of the shape memory closing means placed on the outlet tube.
Figures 3B, 4A, 4B, 5A, 5B:
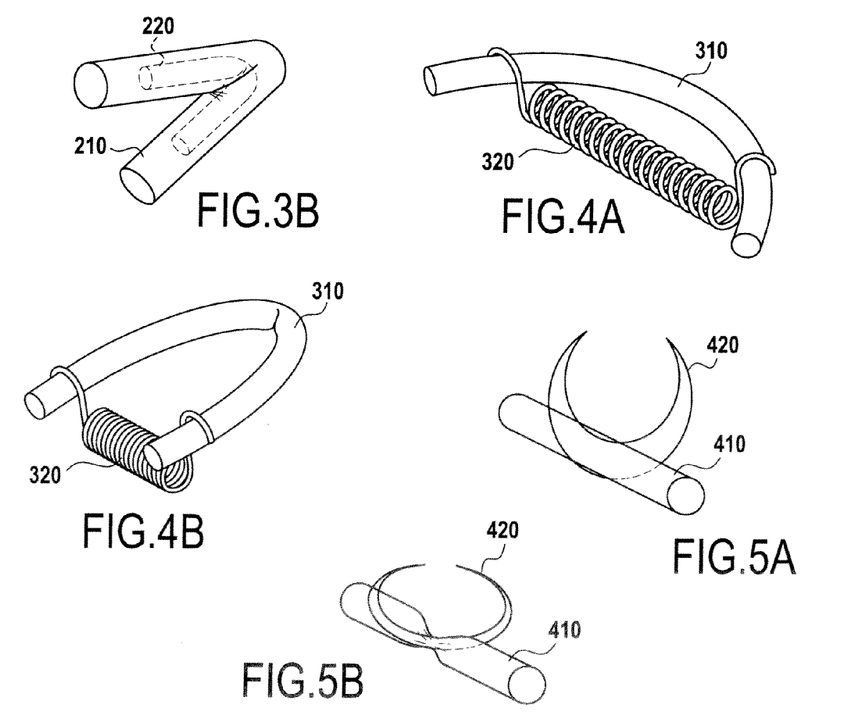
FIG. 4 represents a schematic perspective of another embodiment of the shape memory closing means placed on the outlet tube.
FIG. 5 represents a graphic of a temperature depyrogenation cycle.

In one embodiment, said closing means (220) is a plate or cylinder located inside said outlet tube (210), wherein said plate or cylinder is straight in the open position so that the outlet tube is opened (FIG. 3A), said plate or cylinder presenting one or more angles in a closed position to close the outlet tube (210) (FIG. 3B). In one embodiment, said closing means (320) is a spring fixed at two different locations on the outlet tube (310) (FIG. 4A), wherein said closing means (320) is in a closed position when said spring is in a compressed position to close the outlet tube (310) by pinching or squeezing (FIG. 4B).

In another embodiment, said closing means (420) includes one or more threads or plates in tangential contact with opposite tube outlet (410) outside walls in open position (FIG. 5A). In closed position the tube (410) inside walls are in contact together so no gas may pass through (FIG. 5B).

In the above embodiments, the goal of the closed position is to avoid a gas to pass through the outlet tube.

The packaging outlet has a diameter or a larger section of between 0.1 and 2 cm for letting a gas passing through said outlet. The outlet tube has a size adapted to the outlet size. Typically, the packaging outlet larger section or diameter is of between 1 and 5 mm.

EP 0 201 994 relates to a safety gas container including a valve member made of a shape memory alloy, the valve member having a top head and a bottom head with a stem portion having a relatively small diameter there between. The valve member is fitted in a gas passageway of the container; wherein the shape memory alloy is previously made to remember a smaller shape at a specific temperature; and the valve member is diminished in size in response to a rise in the ambient temperature above the specific temperature so that gaps occurs between the valve member and the inside wall of the gas passageway. However such a valve is obstructing the gas passage and works opposite to the invention. The valve of the prior art works as a decompression valve avoiding overpressure inside the gas container and has a narrow gap of less than 0.1 mm.

US 2006 255064 relates to a fluid storage container comprising a displaceable electrodynamic valve for selectively regulating release of fluid from the container. The displaceable electrodynamic valve is mainly a piezoelectric valve controlled by an external terminal via an electrical lead. Said valve is too complex for the present invention and works using an electric control which should be avoided here.

Besides these both containers (safety gas container or fluid storage container) are not adapted to package containers or vials or other instruments or devices such as prosthesis, implants, surgical or dental materials or instruments. Moreover they are not adapted to a sterilization or depyrogenation step.

In one embodiment of the present invention, the closing means may not be fitted into the outlet tube.

In one embodiment of the invention, said packaging includes a flexible part made of at least one material not degraded at a sterilization or depyrogenation temperature. Such a sterilization or depyrogenation temperature is for example of at least 253° C. Said temperature may be maintained during at least several minutes, typically 20 minutes or more, and preferably 30 minutes or more. The closing temperature is lower than the depyrogenation temperature. The closing temperature is for example comprised between 30° C. and 100° C., for example between 35° C. and 75° C. In one embodiment the closing temperature is comprised between 40 and 65° C. The closing temperature is higher than room temperature which is arbitrary defined to be of 25° C.

In one embodiment, said packaging is made of a material which do not degrade at said sterilization or depyrogenation temperature are selected from the group consisting of a polymer selected from the group of a polyaryletherketone, a PEEK (Poly(ether ether ketone), in particular poly(oxy-1,4-phenylene-oxy-1,4-phenylene-carbonyl-1,4-phenylene); polytetrafluoroethylene (PTFE); a perfluoroalkoxy (PFA) polymer; poly(tetrafluoroethylene-co-perfluoromethyl vinyl ether) (MFA); polyperfluoro(ethylene-co-propylene) (FEP); poly(ethylene-alt-chlorotrifluoroethylene) (ECTFE); poly (ethylene-co-tetrafluoroethylene) (ETFE); poly(vinylidene fluoride) (PDVF); tetrafluoroethylene-co-hexafluoropropylene-co-vinylidene fluoride terpolymer (THV); poly(bisphenol A-co-4-nitrophthalic anhydride-co-1,3-phenylenediamine) (PEI); poly(4-methyl-1-pentene) (PMP); and suitable mixtures thereof.

In one embodiment said sterilization or depyrogenation temperature is of at least 253° C.

Said packaging or tray may be thermoformed. Any form may be used depending on the goal.

In one embodiment said packaging has a dimension of about 20 to 500 mm length, 20 to 500 mm width, and 5 to 300 mm high. Typical dimensions are about 280 mm length, about 280 mm width, and about 30 mm high.

A tray may comprise one or more ergots on its bottom outside surface to fix or position the tray on a surface.

The invention relates to a method for sterilization or depyrogenation of one or more packaged devices, for examples of vials or containers or other instruments or devices such as prosthesis, implants, surgical or dental materials or instruments, placed in said packaging defined according to any embodiment taken alone or in combination.

In one embodiment the invention relates to a method for sterilizing and/or depyrogening vials or containers before there filling, i.e. sterilization or depyrogenation of empty vials or containers. Said vials or containers are packaged without cap.

In one embodiment said method comprises placing into a sterilization or depyrogenation apparatus a packaging made of one or more materials which do not degrade at a sterilization or depyrogenation temperature, said packaging comprising a packaging outlet and an outlet tube connected to said packaging outlet, said outlet tube comprising a proximal end and a distal end, said tube comprising between the proximal end and the distal end a closing means made partly or completely of a shape memory material. In a preferred embodiment, said packaging comprises (or package) one or more packaged devices, for example vials or containers or other instruments or devices such as prosthesis, implants, surgical or dental materials or instruments.

Figure 6:
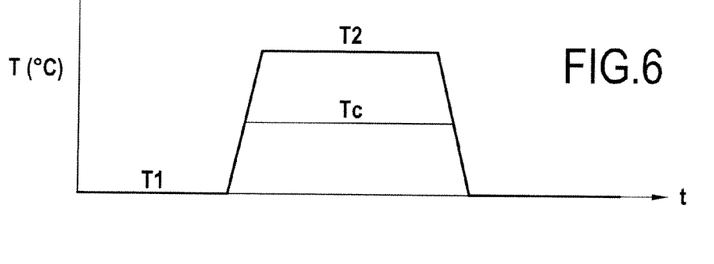
FIG. 6 represents a schematic perspective of another embodiment of the shape memory closing means placed on the outlet tube.

In one embodiment, the method comprises increasing the temperature in the oven from a first temperature T1, (which may be room temperature, i.e. for example 25° C.), wherein said closing means is in a closed position closing the outlet tube, to a second temperature T2 (sterilization or depyrogenation temperature, i.e. for example above 253° C.), wherein said closing means is in an open position to open the outlet tube, maintaining this second temperature T2 for a sufficient period of time to ensure vials or containers sterilization or depyrogenation, decreasing the temperature from the second temperature T2 to a third temperature T3 lower than the closing temperature (Tc) of said closing means to close the outlet tube, and optionally obtaining a partial vacuum in the packaging (FIG. 6). T3 may be the same as T1.

The outlet tube avoids the packaging (bag or tray) explosion due to the gas inflation: The gas present inside said packaging goes through the outlet tube which works as a decompression valve when open. During the temperature decrease, the closing means returns to its initial shape, i.e. in a closed position. Because the closing temperature is higher than the third temperature T3, a partial vacuum may be obtained inside the packaging (bag or tray).

This partial vacuum ensures that the packaging (bag or tray) is sufficiently protecting the packaged device(s), for example vials or containers or other instruments or devices such as prosthesis, implants, surgical or dental materials or instruments from any contamination. If the packaging (bag or tray) is altered, a gas may penetrate the packaging (bag or tray) and the packaged device(s) may be polluted by pyrogens. A skilled person will know before using the packaged device(s) if the sterilization or depyrogenation is correct or not. If the packaged device(s) are still sterile or pyrogen-free, the skilled person will see the correct packaging deflation (due to the vacuum) or hear a noise when opening the packaging (due to the vacuum). Said partial vacuum is generally of between 0.1 and 100 kPa (Low vacuum).

For opening the packaging, in one embodiment, the skilled person will open a bag; in another embodiment, the skilled person will remove the removable sheet or film from the tray. A pre-cut may be made on the packaging to opening it easily.

The invention relates to a packaging obtainable by said method or sterilization or depyrogenation. One goal is to package one or more packaged devices, for example vials or containers or other instruments or devices such as prosthesis, implants, surgical or dental materials or instruments under a partial vacuum to store them after a depyrogenation step and keep them free from pyrogens.

According to one aspect, the invention also relates to a packaging made of one or more materials which do not degrade at a sterilization or depyrogenation temperature said packaging comprising an outlet, and a valve made partly or completely of a shape memory material which changes its shape at a closing temperature Tc higher than room temperature (25° C.), said valve closing the outlet at room temperature and opening a passage for a gas through said outlet when the temperature is above Tc, said packaging being under a partial vacuum when the valve is closed. Said packaging comprises preferably one or more packaged devices, for example vials or containers or other instruments or devices such as prosthesis, implants, surgical or dental materials or instruments. All embodiments disclosed are applicable to this particular aspect of the invention.

According to one aspect, the invention also relates to a packaging of the invention comprising one, two or more packaging areas to package separately one or more packaged devices, for example vials or containers or other instruments or devices such as prosthesis, implants, surgical or dental materials or instruments. In one embodiment, at least two or more packaging areas comprise an outlet wherein said outlets are connected together and forming a main outlet wherein said main outlet comprises a valve made partly or completely of a shape memory material which changes its shape at a closing temperature Tc higher than room temperature (25° C.), said valve closing the main outlet at room temperature and opening a passage for a gas through said main outlet when the temperature is above Tc, said packaging being under a partial vacuum when the valve is closed. In one embodiment, the devices packaged in separate packaging areas of the packaging of the invention are different devices. Typically, the invention may provide a self-assembly device under un-assembled form, wherein different parts to be assembled are located in separate packaging areas. Such self-assembly device may be medical devices or pharmaceutical devices needing to be stored in vacuum.

Figure 7:
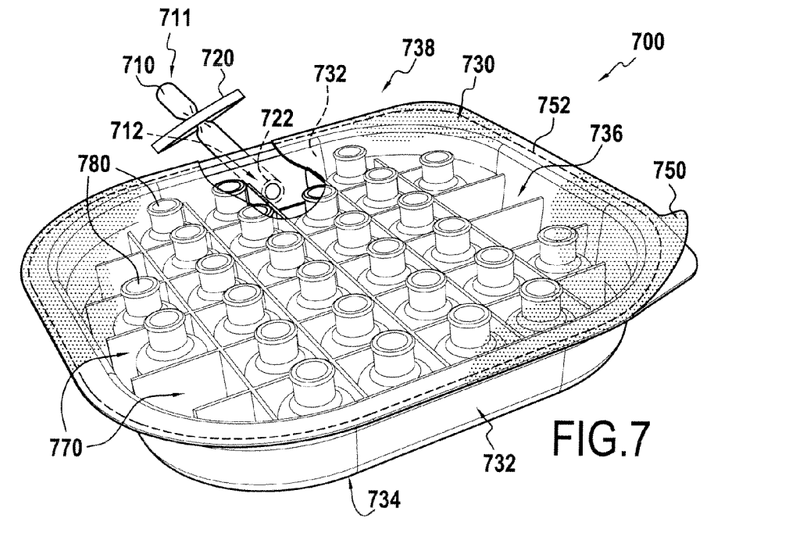
FIG. 7 represents a schematic perspective of one embodiment of the packaging of the invention.

In one embodiment (FIG. 7) said tray or packaging 700 for vials or containers 780, comprises side walls 732, a bottom wall 734 and a completely or partly opened top surface 730 defining an inside packaging area 736 and an outside packaging area 738, wherein at least one wall (732, 734) or top surface 730 comprises an outlet 722 to which is connected an outlet tube 710 to let a gas pass through said outlet 722, wherein said outlet tube 710 comprises a proximal end 711 and a distal end 712, said outlet tube 710 comprising between the proximal end 711 and the distal end 712 a closing means 720 made partly or completely of a shape memory material, said closing means 720 closing the outlet tube 710, said packaging 700 optionally comprising a removable sheet or film 750 placed on the tray top surface 730 to isolate the inside packaging area from the outside packaging area. Said removable sheet or film 750 may be thermosealed along the tray top surface 730 periphery by a continuous or discontinuous thermosealing line 752, said thermosealing being able to preserve a partial vacuum inside said packaging 700. Said tray may be thermoformed using a PEEK polymer. The removable sheet or film 750 may be manufactured in PEEK polymer too.

Figure 8:
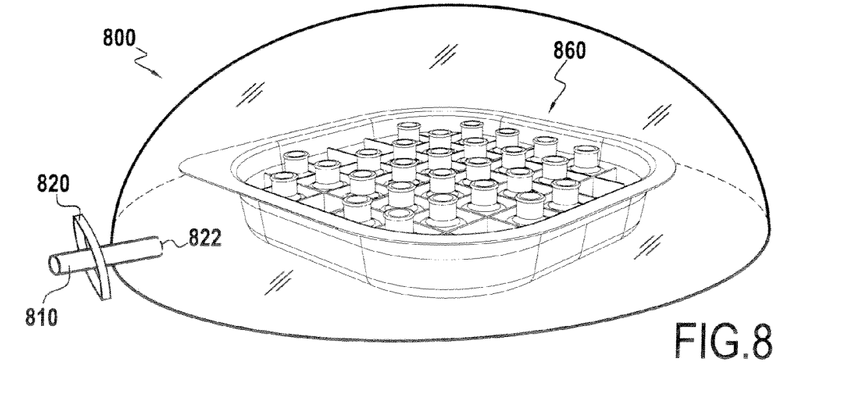
FIG. 8 represents a schematic perspective of another embodiment of the packaging of the invention
Figure 9:
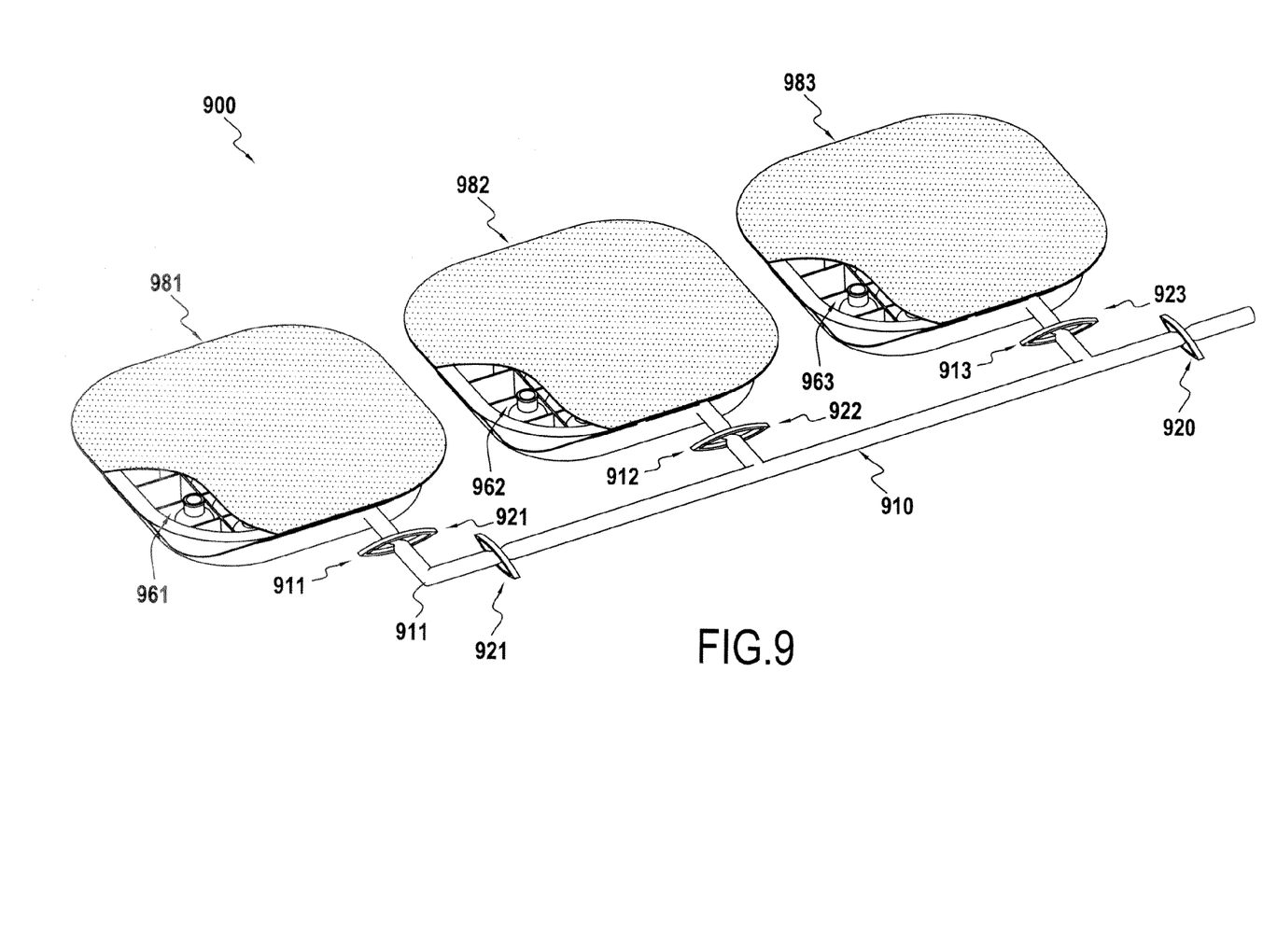
FIG. 9 represents a schematic view of a packaging of he invention comprising a multiple packaging area.

In one embodiment (FIG. 8) a tray 860 made of a material not degrading at a sterilization or depyrogenation temperature such as PEEK is placed in to a bag 800 made of a material not degrading at a sterilization or depyrogenation temperature such as PEEK. Said bag 800 comprises an outlet 722, an outlet tube 810 fixed to said outlet 722 (for example thermosealed) and a closing means 820 according to the invention. FIG. 9 represents a packaging (900) of the invention comprising three packaging areas (981, 982, 983), for packaging separately devices (961, 962, 963), such as trays, vials or containers. The main outlet (910) is open or closed by a main valve made of shape memory material (920). Outlets (911, 912, 913) of each separate packaging area (981, 982, 983) independently comprise optionally separate valves (921, 922, 923) for closing/opening said outlets (911, 912, 913) separately. One or more, and preferably each, of the valves are valves according to the invention (shape memory material).

When not comprising or made of shape memory material the valve (920, 921, 922, 923) is any valve from the market such as an electro-mechanic or electro-pneumatic valve. When separate packaging areas (981, 982, 983) independently comprise separate valves (921, 922, 923), this allows to access independently to devices contained in a specific area (981, or 982, or 983) without influence on the atmosphere or vacuum of other packaging areas (981, or 982, or 983).

Other aims, characteristics and advantages of the invention will appear clearly to the person skilled in the art upon reading the explanatory description which makes reference to the figures which are given simply as an illustration and which in no way limit the scope of the invention.

The figures make up an integral part of the present invention, and any characteristic which appears novel with respect to any prior state of the art from the description taken in its entirety, including the figures, makes up an integral part of the invention in its function and in its generality.

Thus, every figure has a general scope.

The invention claimed is:

1. A packaging made of one or more materials which do not degrade at a sterilization or depyrogenation temperature, said packaging comprising a packaging outlet and an outlet tube connected to said packaging outlet, said outlet tube comprising a proximal end and a distal end, said outlet tube comprising between the proximal end and the distal end a means for closing, made partly or completely of as shape memory material:

wherein said packaging comprises a tray for one or more packaged devices, said tray comprising side walls, a bottom wall and a completely or partly open top surface defining an inside packaging area and an outside packaging area, and wherein at least one wall or top surface comprises the outlet to which is connected the outlet tube to let a gas pass through said outlet, and wherein said packaging is provided with a removable sheet or film placed on the tray top surface to isolate the inside packaging area from the outside packaging area.

2. The packaging of claim 1, wherein said closing means is in a closed position when the temperature is below a reference temperature for closing the outlet tube so that a gas may not penetrate into the packaging through said packaging outlet or in an open position when the temperature is above said reference temperature for allowing a gas passing through the packaging outlet.

3. The packaging of claim 1, wherein said shape memory material is a shape memory alloy.

4. The packaging of claim 1, wherein said packaging is made of a material selected from the group consisting of a polymer selected from the group of a polyaryletherketone, a PEEK (Poly(ether ether ketone), in particular poly(oxy-1,4-phenylene-oxy-1,4-phenylene-carbonyl-1,4-phenylene); polytetrafluoroethylene (PTFE); a perfluoroalkoxy (PFA) polymer; poly(tetrafluoroethylene-co-perfluoromethyl vinyl ether) (MFA); polyperfluoro(ethylene-co-propylene) (FEP); poly(ethylene-alt-chlorotrifluoroethylene) (ECTFE); poly (ethylene-co-tetrafluoroethylene) (ETFE); poly(vinylidene fluoride) (PDVF); tetrafluoroethylene-co-hexafluoropropylene-co-vinylidene fluoride terpolymer (THV); poly(bisphenol A-co-4-nitrophthalic anhydride-co-1,3-phenylenediamine) (PEI); poly(4-methyl-1-pentene) (PMP); and suitable mixtures thereof.

5. The packaging of claim 1, wherein said sterilization or depyrogenation temperature is of at least 253° C.

6. The packaging, of claim 1, wherein said packaging comprises a support area for locating and supporting one or more packaged devices, said support area is provided with separate compartments, wherein each one or more packaged device may be located in a separate compartment.

7. The packaging of claim 1, wherein said closing means is placed at least partially surrounding the outlet tube between said proximal and distal end to close the outlet tube by compression or squeezing, when said closing means is in closed position and when said closing means is in an open position the outlet tube is not compressed or squeezed to let a gas pass through the outlet tube from the proximal end to the distal end.

8. The packaging of claim 1, wherein said closing means in an open position presents a ring, a oval, or a U-shape, or presents a tubular shape surrounding the outlet tube so that the outlet tube is opened, and said closing means, in a closed position, compresses or squeezes the outlet tube to close the outlet tube.

9. The packaging of claim 1, wherein said closing, means is a pink or cylinder located inside said outlet tube, wherein said plate or cylinder is straight in the open position so that the outlet tube is opened, said plate or cylinder presenting one or more angles in a closed position to close the outlet tube.

10. The packaging of claim 1, wherein said closing means is a spring fixed at two different locations on the outlet tube, wherein said closing means is in a closed position when said spring is in a compressed position to close the outlet tube by pinching or squeezing.

11. The packaging of claim 1, comprising one or more packaging areas to package separately one or more packaged devices.

12. The packaging of claim 11, wherein said packaging comprises at least two or more packaging areas each comprising an outlet, wherein said outlets are connected together and forming a main outlet, wherein said main outlet comprises a valve made partly or completely of a shape memory material which changes its shape at a closing temperature Tc higher than room temperature, said valve dosing the main outlet at room temperature and opening a passage for a gas through said main outlet when the temperature is above Tc, said packaging being under a partial vacuum when the valve is closed.

13. The packaging of claim 2, wherein said shape memory material is a shape memory alloy.

14. The packaging of claim 2, wherein said sterilization or depyrogenation temperature is of at least 253° C.

15. The packaging of claim 3, wherein said Sterilization or depyrogenation temperature is of at least 253° C.

16. The packaging, of claim 2, wherein said packaging comprises a support area for locating and supporting one or more packaged devices, said support area is provided with separate compartments, wherein each one or more packaged device may be located in a separate compartment.

17. The packaging of claim 3, wherein said packaging comprises a support area for locating and supporting one or more packaged devices, said support area is provided with separate compartments, wherein each one or more packaged deice may be located in a separate compartment.

18. The packaging of claim 5, wherein said packaging comprises a support area for locating and supporting, one or more packaged devices, said support area is provided with separate compartments, wherein each one or more packaged device may be located in a separate compartment.

19. A packaging made of one or more materials which do not degrade at a sterilization or depyrogenation temperature, said packaging comprising at least two or more packaging areas to package separately one or more packaged devices, said packaging areas each comprising a packaging outlet and an outlet tube connected to said packaging outlet, said outlet tubes comprising a proximal end and a distal end, said outlet tubes comprising between the proximal end and the distal end a means for closing made partly or completely of a shape memory material;
wherein said outlets are connected together and forming a main outlet, wherein said main outlet comprises a valve made partly or completely of a shape memory material which changes its shape at a closing temperature Tc higher than room temperature, said valve closing the main outlet at room temperature and opening a passage for a gas through said main outlet when the temperature is above Tc, said packaging being under a partial vacuum when the valve is closed.

20. The packaging of claim 19, wherein said closing means is in a closed position when the temperature is below a reference temperature for closing the outlet tube so that a gas may not penetrate into the packaging through said packaging outlet or in an open position when the temperature is above said reference temperature for allowing a gas passing through the packaging outlet.

21. The packaging of claim 19, wherein said shape memory material is a shape memory alloy.

22. The packaging of claim 19, wherein said packaging is made of a material selected from the group consisting of a polymer selected from the group of a polyaryletherkelone, a PEEK (Poly(ether ether ketone), in particular poly(oxy-1,4-phenylene-oxy-1,4-phenylene-carbonyl-1,4phenylene); polytetrafluoroethylene (PTFE); a perfluoroalkoxy (PFA) polymer; poly(tetrafluoroethylene-co-perfluoromethyl vinyl ether) (MFA); polyperfluoro(ethylene-co-propylene) (FEP) poly(ethylene-alt-chlorotrifluoroethylene) (ECTFE); poly (ethylene-co-tetrafluoroethylene) (ETFE); poly(vinylidene fluoride) (PDVF); tetrafluoroethylene-co-hexafluoropropylene-co-vinylidene fluoride terpolymer (THV); poly(bisphenol A-co-4-nitrophthalic anhydride-co-1,3-phenylenediamine) (PEI); poly(4-methyl-1-pentene) (PMP); and suitable mixtures thereof.

23. The packaging of claim 19, wherein said sterilization or depyrogenation temperature is of at least 253° C.

24. The packaging of claim 19, wherein at least one of said packaging areas comprises a support area for locating and supporting one or more packaged devices, said support area is provided with separate compartments, wherein each one or more packaged device may be located in a separate compartment.

25. The packaging of claim 19, wherein at least one of said packaging areas is a tray for one or more packaged devices, said tray comprising side walls, a bottom wall and a completely or partly open top surface defining an inside packaging area and an outside packaging area, wherein at least one wall or top surface comprises the packaging outlet to which is connected the outlet tube to let a gas pass through said packaging outlet, wherein said packaging is provided with a removable sheet or film placed on the tray top surface to isolate the inside packaging area from the outside packaging area.

26. The packaging of claim 19, wherein said closing means is placed at least partially surrounding the outlet tube between said proximal and distal end to close the outlet tube by compression or squeezing when said closing means is in closed position and when said closing means is in an open position the outlet tube is not compressed or squeezed to let a gas pass through the outlet tube from the proximal end to the distal end.

27. The packaging of claim 19, wherein said closing means in an open position presents a ring, a oval, or a U-shape, or presents a tubular shape surrounding the outlet tube so that the outlet tube is opened, and said closing means, in a closed position, compresses or squeezes the outlet tube to close the outlet tube.

28. The packaging of claim 19, wherein said closing means is a plate or cylinder located inside said outlet tube, wherein said plate or cylinder is straight in the open position so that the outlet tube is opened, said plate or cylinder presenting one or more angles in a closed position to close the outlet tube.

29. The packaging of claim 19, wherein said closing means is a spring fixed at two different locations on the outlet tube, wherein said closing means is in a closed position when said spring is in a compressed position to close the outlet tube by pinching or squeezing.

30. The packaging of claim 20, wherein said shape memory material is a shape memory alloy.

31. The packaging of claim 20, wherein said sterilization or depyrogenation temperature is of at least 253° C.

32. The packaging of claim 3, wherein said sterilization or depyrogenation temperature is of at least 253° C.

33. The packaging of claim 20, wherein at least one of said packaging areas comprises a support area for locating and supporting one or more packaged devices, said support area is provided with separate compartments, wherein each one or more packaged device may be located in a separate compartment.

34. The packaging of claim 21, wherein at least one of said packaging areas comprises a support area for locating and supporting one or more packaged devices, said support area is provided with separate compartments, wherein each one or more packaged device may be located in a separate compartment.

35. The packaging of claim 23, wherein at least one of said packaging areas comprises a support area for locating and supporting one or more packaged devices, said support area is provided with separate compartments, wherein each one or more packaged device may be located in a separate compartment.

36. The packaging of claim 20, wherein at least one of said packaging areas is a tray for one or more packaged devices, said tray comprising side walls, a bottom wall and a completely or partly open top surface defining an inside packaging area and an outside packaging area, wherein at least one wall or top surface comprises the outlet to which is connected the outlet tube to let a gas pass through said outlet, wherein said packaging is provided with a removable sheet or film placed on the tray top surface to isolate the inside packaging area from the outside packaging area.

* * * * *

UNITED STATES PATENT AND TRADEMARK OFFICE
CERTIFICATE OF CORRECTION

PATENT NO. : 8,950,579 B2  Page 1 of 1
APPLICATION NO. : 13/257554
DATED : February 10, 2015
INVENTOR(S) : Zambaux It is certified that error appears in the above-identified patent and that said Letters Patent is hereby corrected as shown below:

In the claims
Column 8, line 27, please delete "," after closing.
Column 8, line 27, please replace "as" with -- a --.
Column 8, line 28, please replace ":" with -- ; --.
Column 8, line 65, please delete "," after packaging.
Column 9, line 6, please delete "," after squeezing.
Column 9, line 17, please delete "," after closing.
Column 9, line 18, please replace "pink" with -- plate --.
Column 9, line 36, please replace "dosing" with -- closing --.
Column 9, line 45, please replace "Sterilization" with -- sterilization --.
Column 9, line 47, please delete "," after packaging.
Column 9, line 56, please replace "deice" with -- device --.
Column 9, line 58, please delete "," after supporting.
Column 10, line 25, please replace "polyaryletherkelone" with -- polyaryletherketone --.
Column 10, line 27, please replace "4phenylene" with -- 4-phenylene --.

Signed and Sealed this
Twenty-sixth Day of January, 2016

Michelle K. Lee
*Director of the United States Patent and Trademark Office*